United States Patent
Mahlin

(10) Patent No.: US 8,469,944 B2
(45) Date of Patent: Jun. 25, 2013

(54) INTRODUCER ACCESS ASSEMBLY

(75) Inventor: Fredrik Mahlin, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 157 days.

(21) Appl. No.: 12/611,277

(22) Filed: Nov. 3, 2009

(65) Prior Publication Data

US 2011/0106097 A1    May 5, 2011

(51) Int. Cl.
*A61M 25/18* (2006.01)
*A61M 25/01* (2006.01)

(52) U.S. Cl.
USPC .......................................... 604/533; 606/108

(58) Field of Classification Search
USPC ............... 606/108; 604/93.01, 200, 244, 164, 604/164.01–164.09, 264, 523, 533–535, 604/284
See application file for complete search history.

(56) References Cited

U.S. PATENT DOCUMENTS

| | | | |
|---|---|---|---|
| 4,931,049 A | 6/1990 | Klimas | |
| 4,988,356 A | 1/1991 | Crittenden et al. | |
| 5,687,727 A * | 11/1997 | Kraus et al. | 604/161 |
| 6,363,273 B1 * | 3/2002 | Mastrorio et al. | 604/161 |
| 6,524,304 B1 * | 2/2003 | Picou et al. | 604/539 |
| 7,740,616 B2 * | 6/2010 | Smith et al. | 604/174 |
| 2002/0123755 A1 * | 9/2002 | Lowe et al. | 606/108 |
| 2004/0204741 A1 | 10/2004 | Egnelov et al. | |
| 2005/0021004 A1 * | 1/2005 | Cully et al. | 604/528 |

FOREIGN PATENT DOCUMENTS

WO    WO 2006/065470 A1    6/2006

OTHER PUBLICATIONS

U.S. Appl. No. 13/505,321, filed May 1, 2012, Mahlin.

* cited by examiner

*Primary Examiner* — Kathleen Holwerda
*Assistant Examiner* — Sarah W Aleman
(74) *Attorney, Agent, or Firm* — Foley & Lardner LLP

(57) ABSTRACT

An elongated introducer access assembly 2 comprising a distal end 4 and a proximal end 6, and provided with a first tubular channel 8 having a longitudinal axis 10 and running from a first proximal end opening 12 to a distal end opening (14) of the assembly and being adapted to receive a first tubular medical device. The assembly is provided with a second tubular channel 16 having a second proximal end opening 18 and running from the proximal end of the assembly. The second tubular channel being arranged in an angled direction in relation to the longitudinal axis of the first tubular channel, and that the second tubular channel enters the first tubular channel at a junction (20) proximally to the distal end of the assembly, and that an intersectional angle ($\alpha$) is formed between the first tubular channel and the second tubular channel. The assembly further comprises a cutting unit 22 adapted to provide an opening cut through a part of a first tubular medical device arranged in said first tubular channel such that a second tubular device may be inserted into said second tubular channel and into the first tubular medical device via said opening cut.

18 Claims, 2 Drawing Sheets

INTRODUCER ACCESS ASSEMBLY

FIELD OF THE INVENTION

The present invention relates to an introducer access assembly, and a method of using such assembly.

BACKGROUND OF THE INVENTION

A medical introducer is generally used to gain access to internal organs in order to introduce another medical device into the body. Within the scope of the present invention the other medical device may typically be a pressure sensor catheter inserted into arteries, inter alia to measure blood pressure within arteries, e.g. in coronary vessels, in order to detect and localize constrictions.

When such a measurement procedure is terminated the medical device is withdrawn, the introducer is maintained in place, and it is sometimes required to close and properly seal the artery. In that case a closing device may be inserted into the vessel in order to close the incision through the vessel wall.

Introducers from different manufacturers might vary considerably in shape, length, structure etc.

In particular the proximal end of the introducer may have very different structures.

During the above-described procedure when performing pressure measurements within the body there is an overall requirement, both from the patient and the physician, that the whole procedure should be as smooth as possible.

During insertion of a closing device it is considered important to be able to easily and correctly gain access to the lumen of the introducer in order to insert the closing device.

SUMMARY OF THE INVENTION

The inventor has realised that a more streamlined procedure, both for the patient and for the physician is achieved if the introducer, already inserted into the patient, is maintained and used as a guide to the introducer required to perform e.g. insertion of a closing device.

Thus, the object of the present invention is to achieve an introducer assembly enabling a more user-friendly procedure that is safe to use for the patient.

Thus, the present invention relates to an elongated introducer access assembly comprising a distal end and a proximal end, and provided with a first tubular channel having a longitudinal axis and running from a first proximal end opening to a distal end opening of said assembly and being adapted to receive a tubular medical device. The assembly is provided with a second tubular channel having a second proximal end opening running from the proximal end of the assembly, said second tubular channel being arranged in an angled direction in relation to the longitudinal axis of the first tubular channel, and that the second tubular channel enters the first tubular channel at a junction proximally to the distal end of the assembly, and that an intersectional angle is formed between the first tubular channel and the second tubular channel, wherein the assembly further comprises a cutting unit adapted to provide an opening cut through a part of a first tubular medical device arranged in said first tubular channel such that a second tubular device may be inserted into said second tubular channel and into the first tubular medical device via said opening cut.

By use of the present invention an opening cut is achieved in the introducer wall in a controlled and safe way such that a tubular medical device may be guided and inserted into a vessel in a safe and controlled manner.

The tubular medical device may be e.g. another introducer specifically designed to receive e.g. a closing device as described above.

It will then be necessary to gain access to the lumen of the introducer, which is achieved, by use of the present invention, by making an opening cut in the wall of the introducer through which opening cut the new introducer may be inserted into the introducer and then further to a desired position.

One further advantage of the present invention is that the access assembly may function as a handle when the second tubular medical device is inserted into the introducer during the following procedure, e.g. the closing of a vessel.

SHORT DESCRIPTION OF THE APPENDED DRAWINGS

DETAILED DESCRIPTION OF PREFERRED EMBODIMENTS OF THE INVENTION

The present invention will now be described in detail with references to the appended drawings.

Figure 1A:
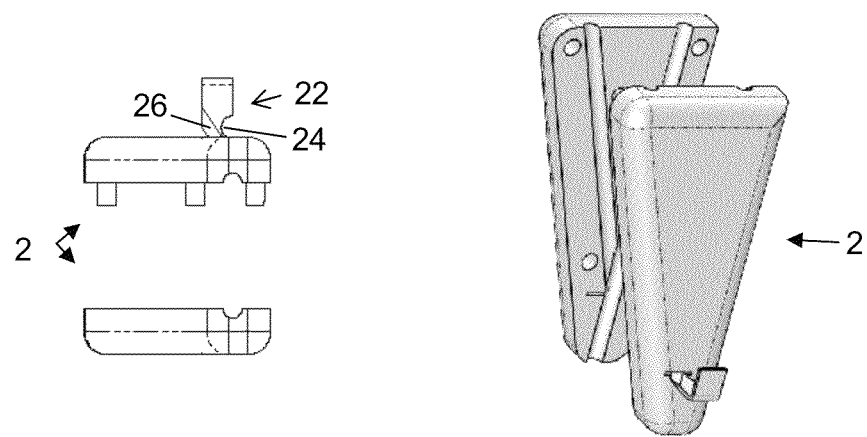
FIGS. 1a and 1b show different views of the introducer access assembly according to the present invention.

FIG. 1a shows, to the right, a perspective view of the assembly, and to the left a view from the distal side.

Figure 1B:
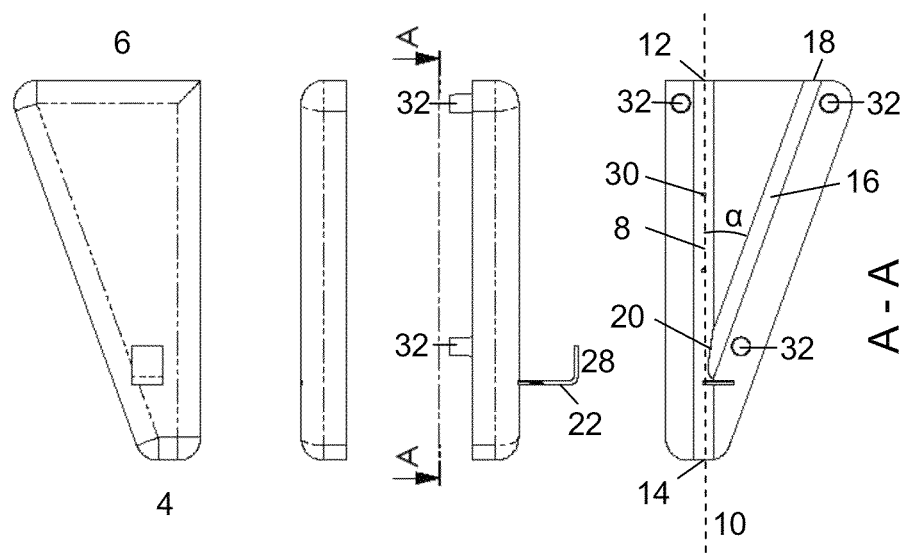

FIG. 1b shows, from left to right, a side view where the distal end of the assembly is down in the figure, a top view showing the two halves of the assembly in a disassembled state, and a side view along A-A showing the inner side of one of the halves.

With references to FIGS. 1a and 1b the present invention relates to an elongated introducer access assembly 2 comprising a distal end 4 and a proximal end 6, and provided with a first tubular channel 8, having a longitudinal axis 10, and running from a first proximal end opening 12 to a distal end opening 14 of the assembly and being adapted to receive a first tubular medical device (not shown).

The assembly is provided with a second tubular channel 16 having a second proximal end opening 18 running from the proximal end of the assembly. The second tubular channel is arranged in an angled direction in relation to the longitudinal axis of the first tubular channel.

The second tubular channel enters the first tubular channel at a junction 20 proximally to the distal end of the assembly. An intersectional angle is formed between the first tubular channel and the second tubular channel. The angle is indicated as α in the figure.

The inner diameters of the tubular channels are naturally related to the outer diameters of the tubular devices to be arranged in the channels, preferably such that a steady fit is achieved for the device arranged in the first channel and that the second tubular medical device may easily be inserted into the second channel but at the same time be securely guided into the channel and into the first tubular device in the first channel via the opening cut.

The assembly further comprises a cutting unit 22 adapted to provide an opening cut through a part of a first tubular medical device arranged in said first tubular channel such that a second tubular device may be inserted into the second tubular channel and into the first tubular medical device via the opening cut.

Preferably, the cutting unit has a flat structure to be inserted into the assembly via a mating slit in the assembly. In one embodiment, the cutting unit is arranged in the slit in one of the halves of the assembly and when the halves are assembled around an introducer the cutting unit is pushed into the assembly resulting in that an opening cut is made in the introducer and the edge part of the cutting unit then continues into the opposing half where it is accommodated. The size of the cutting unit must be such that when fully inserted into the assembly no part exists at the other side of the assembly.

The cutting edge has preferably a razor blade structure and is made from metal, e.g. stainless steel. It may also be possible to achieve a cutting edge in other materials, e.g. certain plastic materials.

The cutting unit is arranged at a location distally to the junction and comprises a recess 24 adapted to accommodate a first tubular medical device arranged in the first tubular channel when the cutting unit is fully pushed into the assembly. Preferably, the recess has a semicircular shape. The cutting unit is arranged such that the opening cut is essentially perpendicular to the longitudinal axis of the first tubular channel and the cutting edge 26 (partly seen in FIG. 1a) is arranged such that it cuts through at least ½ and up to approximately ¾ of the diameter of a first tubular medical device arranged in the first tubular channel. The exact size of the opening cut is naturally dependent upon the diameter of the second tubular device to be inserted into the introducer via the second tubular channel and opening cut.

The cutting unit further comprises a pushing means 28 arranged at the outside of the assembly for moving the cutting unit into the housing in order to provide said opening cut.

The intersectional angle $\alpha$, i.e. the angle between the first and second tubular channels, is less than 45°, preferably in the interval of 20° and 40°. The angle must not be too small in that then it would be difficult for the second tubular medical device to enter the opening cut. On the other hand, if the angle is too large, it would also be difficult for the second tubular medical device to enter the opening, and the insertion may also be hindered if the bend at the junction is too sharp.

In the shown embodiment the first tubular channel is straight and the second tubular channel is also straight but forms an angled channel together with the distal part of the first tubular channel distally to the junction.

An obvious reason for the first tubular channel being straight is that it is easy to arrange the assembly around e.g. an introducer. One might naturally also consider a variant where the axis of the first tubular channel is slightly curved and also the second channel being slightly curved, the channels may then approximate the letter "Y". Also combinations where one of the channels is curved and the other is straight is also possible.

According to a preferred embodiment the assembly comprises at least one fixation member 30 arranged at the inner surface of the first tubular channel adapted to fixate the first tubular medical device arranged in the first tubular channel in the longitudinal direction. Preferably, the fixation member is arranged proximally to the junction. The fixation member may be in the form of a protrusion, a short pin, or a track or consists of an inert or rough material at the inner surface of the first tubular channel.

As shown in the figures the assembly comprises two halves adapted to be assembled and positioned such that a tubular medical device may be arranged in the first channel, and also adapted to be separated from each other. In the figures one embodiment is illustrated where the two halves are two non-connected parts when the assembly is in its non-assembled state. In another embodiment the two halves are connected to each other by at least one hinge (not shown). The hinge or hinges may be arranged at one of the longer sides of the assembly such that the assembly may be folded around the introducer to be arranged in the first channel.

The assembly is further provided with mating means 32 for fastening and orientating the two halves in relation to each other during assembling. The mating means may comprise a number of extending pins at one half of the assembly and mating depressions/holes at the other half to receive the pins such that a frictional connection is achieved.

Preferably the assembly is a separate device that is attached to an introducer when desired. However, according to another embodiment the assembly instead is integrated with a tubular medical device arranged in the second channel.

In a typical use of the assembly the first tubular medical device to be arranged in the first tubular channel is an introducer used e.g. when inserting measurement catheters into the body, e.g. via artery vessels. In such a use of the assembly the second tubular device to be inserted into the second tubular channel and into the tubular medical device via the opening cut is a so-called closure device used to seal and close a vessel inside the body.

Preferably the assembly essentially is made from plastic, but other materials may also be possible, e.g. metal, combinations of metal and plastic.

Advantageously, the assembly is a disposable device, and must be possible to sterilize prior use.

Figure 2:
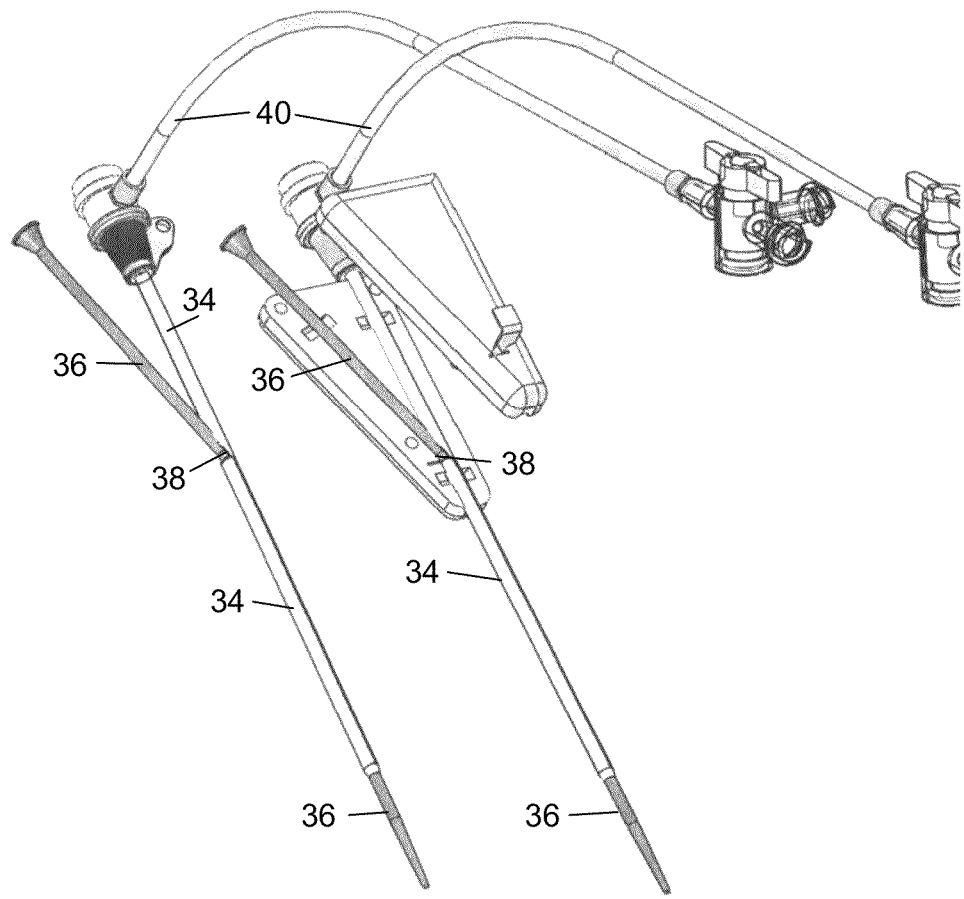
FIG. 2 illustrates the use of the introducer access assembly according to the present invention.

FIG. 2 illustrates the use of the assembly according to the present invention. To the right in the figure the two halves of the assembly are shown when the halves are disconnected from each other after an opening cut is achieved in an introducer 34 and tubular medical device 36 being inserted into the opening cut 38.

To the left in the figure the introducer is shown having a tubular medical device inserted into the opening cut. In the figure is also shown a tubular arrangement 40 connected to the proximal end of the introducer 34.

The invention also relates to a method of using an elongated introducer access assembly (2) comprising a distal end (4) and a proximal end (6), and provided with a first tubular channel (8) having a longitudinal axis (10) and running from a first proximal end opening (12) to a distal end opening (14) of said assembly and being adapted to receive a first tubular medical device, the assembly is provided with a second tubular channel (16) having a second proximal end opening (18) and running from the proximal end of the assembly, said second tubular channel being arranged in an angled direction in relation to the longitudinal axis of the first tubular channel, and that the second tubular channel enters the first tubular channel at a junction (20) proximally to the distal end of the assembly, and that an intersectional angle ($\alpha$) is formed between the first tubular channel and the second tubular channel.

The method comprises:
providing a first tubular medical device in said first channel, providing an opening cut through a part of the first tubular medical device by a cutting unit (22),
inserting a second tubular device into said second tubular channel and into the first tubular medical device via said opening cut.

The cutting unit comprises a cutting edge (26) that is arranged such that it cuts through at least ½, up to a maximum of ¾ of the diameter of the first tubular medical device arranged in said first tubular channel.

In addition the cutting unit comprises a pushing means (28) arranged at the outside of the assembly for moving the cutting unit in a direction essentially perpendicular to the longitudinal axis of first tubular channel and into the housing in order to provide said opening cut. The cutting unit is moved until a stopping means (not shown), e.g. an angled part of the pushing means, is in contact with the outer surface of the assembly and remains there during the insertion of the second tubular device.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. An elongated introducer access assembly comprising:
   a distal end and a proximal end,
   a first tubular channel having a longitudinal axis and running from a first proximal end opening to a distal end opening of said assembly and being adapted to receive a first tubular medical device,
   a second tubular channel having a second proximal end opening and running from the proximal end of the assembly, said second tubular channel being arranged in an angled direction in relation to the longitudinal axis of the first tubular channel such that a plane is defined by the second tubular channel, the first tubular channel, and an intersection of the second tubular channel and the first tubular channel, and
   a cutting unit adapted to provide an opening cut through a part of the first tubular medical device arranged in the first tubular channel, such that a second medical device may be inserted into said second tubular channel and into the first tubular medical device via said opening cut,
   wherein the cutting unit is configured to move in a direction transverse to the plane to provide the opening cut,
   wherein the second tubular channel enters the first tubular channel at a junction proximally to the distal end of the assembly, and an intersectional angle is formed between the first tubular channel and the second tubular channel, and
   wherein the assembly comprises a first half and a second half adapted to separate from the first half, the first and second halves being adapted to receive, when assembled together, the first tubular medical device in the first tubular channel.

2. Introducer access assembly according to claim 1, wherein the cutting unit is arranged at a location distally to the junction.

3. Introducer access assembly according to claim 1, wherein the cutting unit comprises a recess adapted to accommodate the first tubular medical device arranged in said first tubular channel.

4. Introducer access assembly according to claim 3, wherein the recess has a semicircular shape.

5. Introducer access assembly according to claim 1, wherein the cutting unit is arranged such that the opening cut is essentially perpendicular to the longitudinal axis of said first tubular channel.

6. Introducer access assembly according to claim 1, wherein the cutting unit comprises a cutting edge that is arranged such that it cuts through at least ½ of the diameter of the first tubular medical device arranged in said first tubular channel.

7. Introducer access assembly according to claim 1, wherein the cutting unit comprises a cutting edge that is arranged such that it cuts through a maximum of ¾ of the diameter of the first tubular medical device arranged in said first tubular channel.

8. Introducer access assembly according to claim 1, wherein the cutting unit comprises a handle arranged at the outside of the assembly for moving the cutting unit into a housing of the assembly in order to provide said opening cut.

9. Introducer access assembly according to claim 1, wherein the intersectional angle is less than 45°.

10. Introducer access assembly according to claim 1, further comprising at least one fixation member arranged at an inner surface of the first tubular channel and adapted to fixate the first tubular medical device arranged in said first tubular channel in the longitudinal direction.

11. Introducer access assembly according to claim 10, wherein said at least one fixation member is in the form of a protrusion, a short pin, or a track or comprises an inert or rough material.

12. Introducer access assembly according to claim 1, wherein said first half and said second half are connected to each other by at least one hinge.

13. Introducer access assembly according to claim 1, wherein the assembly further comprises a fastener adapted to fasten and orient said first half and said second half in relation to each other during assembling.

14. Introducer access assembly according to claim 1, wherein the assembly is integrated with the medical device arranged in the second tubular channel.

15. Introducer access assembly according to claim 1, wherein the cutting unit includes a cutting edge configured to move in a direction transverse to the longitudinal axis of the first tubular channel to provide the opening cut.

16. Introducer access assembly according to claim 1, wherein the cutting unit includes a cutting edge, and the cutting edge comprises a recess adapted to accommodate the first tubular medical device arranged in said first tubular channel.

17. Introducer access assembly according to claim 16, wherein the recess has a semicircular shape.

18. Introducer access assembly according to claim 1, wherein the cutting unit includes a blade to provide the opening cut, and the blade is arranged such that the opening cut is elongated and the elongated opening cut is essentially perpendicular to the longitudinal axis of said first tubular channel.

* * * * *